(12) United States Patent
Murphy (10) Patent No.: US 8,583,387 B2
(45) Date of Patent: Nov. 12, 2013

(54) ULTRASONIC LEVEL, ON-BOARD DIAGNOSTIC ASSESSMENT

(75) Inventor: Gregory Paul Murphy, Janesville, WI (US)

(73) Assignee: SSI Technologies, Inc., Janesville, WI (US)

( * ) Notice: Subject to any disclaimer, the term of this patent is extended or adjusted under 35 U.S.C. 154(b) by 251 days.

(21) Appl. No.: 13/070,850

(22) Filed: Mar. 24, 2011

(65) Prior Publication Data

US 2011/0301883 A1 Dec. 8, 2011

Related U.S. Application Data

(60) Provisional application No. 61/351,689, filed on Jun. 4, 2010.

(51) Int. Cl.
*G01F 17/00* (2006.01)

(52) U.S. Cl.
USPC ............... 702/55; 702/45; 702/46; 702/54

(58) Field of Classification Search
USPC .......................... 702/45–46, 54–55
See application file for complete search history.

(56) References Cited

U.S. PATENT DOCUMENTS

| | | |
|---|---|---|
| 4,158,964 A | 6/1979 | McCrea et al. |
| 4,310,906 A | 1/1982 | Cantrell, Jr. et al. |
| 4,388,828 A | 6/1983 | Dougherty |
| 4,451,894 A | 5/1984 | Dougherty et al. |
| 4,531,406 A | 7/1985 | Fritz |
| 4,815,323 A | 3/1989 | Ellinger et al. |
| 4,853,694 A | 8/1989 | Tomecek |
| 4,984,449 A * | 1/1991 | Caldwell et al. ............... 73/49.2 |
| 5,179,926 A | 1/1993 | Ament |
| 5,182,523 A | 1/1993 | Ertel et al. |
| 5,309,763 A | 5/1994 | Sinclair |
| 5,319,973 A | 6/1994 | Crayton et al. |
| 5,363,314 A | 11/1994 | Kobayashi et al. |

(Continued)

FOREIGN PATENT DOCUMENTS

| | | |
|---|---|---|
| EP | 1770815 | 4/2007 |
| EP | 1785700 | 5/2007 |
| WO | 0184090 | 11/2001 |
| WO | 2005036105 | 4/2005 |

OTHER PUBLICATIONS

PCT/US2011/038161 International Search Report and Written Opinion dated Sep. 2, 2011 (5 pages).

(Continued)

*Primary Examiner* — Mischita Henson
(74) *Attorney, Agent, or Firm* — Michael Best & Friedrich LLP (57) ABSTRACT

A system and method for performing a diagnostic assessment of an ultrasonic sensor that measures a fluid level. A PWM signal is generated based on a reflection of an ultrasonic signal output by the ultrasonic sensor. The PWM has a period, and a plurality of pulses. Each pulse encodes a predetermined parameter and has a width. The PWM signal encodes the fluid level, fluid temperature, fluid speed of sound, and a status of the ultrasonic transducer. The PWM signal is received at a processor. The processor performs the diagnostic assessment of the ultrasonic sensor based on the period of the PWM signal and the widths of the plurality of pulses of the PWM signal. The processor is able to detect time reference shifts by assessing the PWM signal.

17 Claims, 6 Drawing Sheets

(56) References Cited

U.S. PATENT DOCUMENTS

| | | | |
|---|---|---|---|
| 5,644,299 | A | 7/1997 | Cruickshank |
| 5,765,433 | A | 6/1998 | Johnson |
| 5,892,315 | A | 4/1999 | Gipson et al. |
| 6,157,894 | A | 12/2000 | Hess et al. |
| 6,215,226 | B1 | 4/2001 | Durkee |
| 6,250,137 | B1 | 6/2001 | Takahashi et al. |
| 6,427,532 | B1 | 8/2002 | Keller |
| 6,460,402 | B1 | 10/2002 | Gomm et al. |
| 6,484,088 | B1 * | 11/2002 | Reimer .................... 701/123 |
| 6,568,281 | B1 | 5/2003 | Sato et al. |
| 6,573,732 | B1 | 6/2003 | Reimer |
| 6,595,071 | B1 | 7/2003 | Doten |
| 6,675,646 | B2 * | 1/2004 | Nishihara .................. 73/290 V |
| 6,886,412 | B2 | 5/2005 | Banno et al. |
| 6,925,869 | B2 | 8/2005 | Senibi et al. |
| 6,951,131 | B2 | 10/2005 | Sawert et al. |
| 6,968,738 | B2 | 11/2005 | Atkinson |
| 6,993,967 | B2 | 2/2006 | Forgue |
| 7,248,089 | B2 | 7/2007 | Pedersen et al. |
| 7,370,527 | B2 | 5/2008 | Miyagawa |
| 7,406,871 | B2 | 8/2008 | Sugiura |
| 7,520,180 | B2 | 4/2009 | Deutscher et al. |
| 7,542,870 | B2 | 6/2009 | Reimer et al. |
| 7,583,562 | B2 | 9/2009 | Lyon |
| 7,761,271 | B2 * | 7/2010 | Giehrl et al. .................... 703/13 |
| 2003/0069684 | A1 * | 4/2003 | Reimer .................... 701/123 |
| 2006/0062291 | A1 * | 3/2006 | Marotta et al. ................ 375/238 |
| 2009/0199626 | A1 | 8/2009 | Murphy et al. |
| 2010/0102672 | A1 | 4/2010 | Hoffman et al. |

OTHER PUBLICATIONS

AT-AN4: ACU-TRAC, "Fuel Level Sensor Product Overview," author SSI, published Mar. 19, 2007 (9 pages).
"Ultrasonic Tank Sensor," taken from (http://www.philippi-online.de/index.php5?url=produkte.php5&m1id=2&sprache=en&kat1) on Jun. 16, 2010 (2 pages).
Customer Product Webpage: ACU-TRAC, "Ultrasonic Fuel Level Sensor," (http://www.ssitechnologies.com/fuel.htm), author SSI, available at least since Jun. 17, 2010 (1 page).
Distributor Product Webpage: ACU-TRAC, "Ultrasonic Tank Sensor," (http://www.info.philippi-online.de/neuheiten09_en.pdf), author Philippi, available at least since Jun. 17, 2010 (5 pages).
PCT/US2011/038161 International Preliminary Report on Patentability and Written Opinion date of mailing Dec. 13, 2012 (6 pages).

* cited by examiner

ULTRASONIC LEVEL, ON-BOARD DIAGNOSTIC ASSESSMENT

RELATED APPLICATIONS

The present patent application claims priority to U.S. Provisional Patent Application Ser. No. 61/351,689 filed Jun. 4, 2010. The entire contents which are herein incorporated by reference.

BACKGROUND

The present invention relates to ultrasonic sensors and, more particularly to the diagnostic assessment of such sensors.

Ultrasonic transducers can be used to measure a distance to the surface of a liquid. In some situations, a transducer is positioned at the top of a tank for a liquid, such as the fuel tank of an automobile, truck, or other vehicle. An ultrasonic signal is generated by the transducer and the time it takes for the signal to travel from the top of the tank to the surface of the fuel, reflect off the surface of the fuel, and return to the transducer is measured. If certain information about the tank is known, such as its volume or dimensions, the time measurement can be used in a calculation to determine how much fuel is in the tank. Ultrasonic technology for use in determining the type of fuel in a fuel tank has also been developed, including the technology disclosed in commonly assigned U.S. application Ser. No. 12/027,512.

SUMMARY

Outside of the field of ultrasonic sensing, a number of regulations related to diagnostic requirements for electronic vehicle systems have been promulgated. These regulations include Title 13, California Code Regulations, Section 1968.2, entitled "Malfunction and Diagnostic System Requirements for 2004 and Subsequent Model-Year Passenger Cars, Light-Duty Trucks, and Medium-Duty Vehicles and Engines (OBD II)." This regulation relates to vehicles with diesel engines. In some modern diesel-engine vehicles, liquid catalysts are used in exhaust systems to reduce exhaust emissions. Part of the regulation requires the detection of malfunctions such as the presence of an incorrect catalyst or an insufficient amount of the catalyst.

The inventors have recognized that ultrasonic technology can be used to detect the presence of liquid catalysts and malfunctions or error conditions in catalyst systems (such as circumstances where an insufficient amount of or an incorrect catalyst is present) and have developed technology that evaluates a pulse width modulated ("PWM") signal to determine the presence of malfunctions.

The invention provides, among other things, a method to detect a time reference shift failure of a sensor using a PWM output. The invention also provides a method to provide a level measurement of a fluid that has enhanced immunity to time reference shifts using an ultrasonic sensor with PWM output. The invention also provides a method to calculate a specific gravity measurement of a fluid that has enhanced immunity to time reference shifts using an ultrasonic sensor with a PWM output.

In one implementation, the invention provides an ultrasonic sensor system having an ultrasonic sensor. The ultrasonic sensor includes a microcontroller, a transducer, a temperature sensor, and a driver. The transducer is electrically connected to the microcontroller and is configured to generate an ultrasonic signal and to receive a reflection of the ultrasonic signal from a surface of a fluid. The temperature sensor is electrically connected to the microcontroller and is configured to generate a temperature signal indicative of a temperature of the fluid. The driver is electrically connected to the microcontroller and is configured to output a pulse-width modulated (PWM) signal based on the temperature signal and the reflection. The PWM signal includes a period, and a plurality of pulses. Each pulse encodes a predetermined parameter and has a width. A diagnostic assessment of the sensor may be performed by evaluating the PWM signal in, for example, a processor connected to the microcontroller. The timing and sequence of pulses in the PWM is evaluated. Additional testing may be performed on the signal 42 based on the time of the pulses. The time of each pulse may be examined to determine whether the time (or width) of the pulses is plausible as compared to predetermined constraints or parameters.

A method of performing diagnostics on an ultrasonic sensor that measures a level of a fluid can be carried out by generating, by a transducer, an ultrasonic signal and receiving, via the transducer, a reflection of the ultrasonic signal. A microcontroller calculates a time-of-flight based on a time elapsed between generating the ultrasonic signal and receiving the reflection. The microcontroller further receives a temperature signal from a temperature sensor that indicates a temperature of the fluid. A pulse-width modulated (PWM) signal is generated based on the time-of-flight and the temperature signal. The PWM signal includes a first pulse encoding the level of the fluid, and a second pulse encoding a status of the ultrasonic sensor. A diagnostic assessment of the sensor is performed by evaluating the timing of the pulses of the PWM signal.

The invention also provides another method of assessing an ultrasonic sensor that measures a fluid level. The method includes receiving, by a processor, a PWM signal output by the ultrasonic sensor. The PWM signal includes a first pulse encoding a level of a fluid based on a time of flight of an ultrasonic signal through the fluid and based on a temperature of the fluid. The PWM signal also includes a second pulse encoding a status of the ultrasonic sensor. The method further includes the processor performing the diagnostic assessment of the ultrasonic sensor using the PWM signal.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
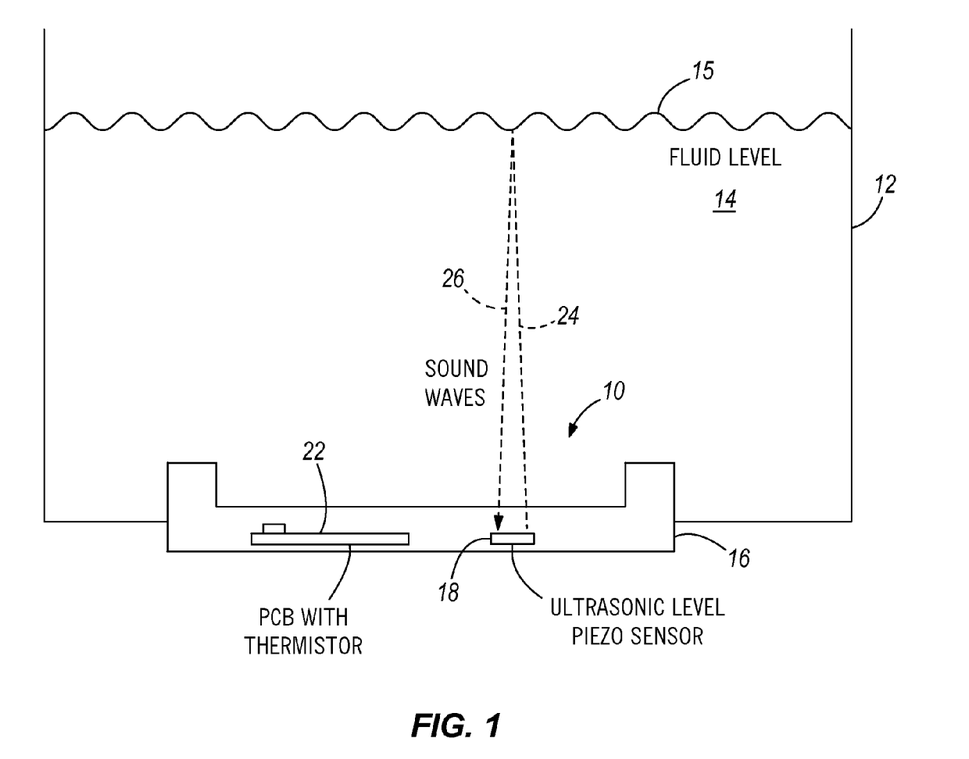
FIG. 1 is a schematic illustration of an ultrasonic level sensor placed at the bottom of a liquid or fluid container or tank and illustrating the transmission and reflection of sound waves from and to a piezoelectric transducer of the sensor.

FIG. 1 illustrates an ultrasonic level sensor 10 positioned at the bottom of a tank 12 or similar container filled with a fluid 14, such as a diesel exhaust fluid ("DEF") (e.g., AdBlue liquid), having a top surface 15. The ultrasonic level sensor 10 includes a housing 16, a piezoelectric transducer 18, and a printed circuit board 22 with a thermistor and other components (which are described below). A signal from a microcontroller or similar device (which may be amplified or otherwise conditioned by a driver circuit) is provided to the transducer 18. The transducer 18 generates an ultrasonic sound wave (represented by dashed line 24) that propagates through the fluid 14 to the surface 15. At least a portion of the sound wave (represented by dashed line 26) is reflected from the surface 15 back to the transducer 18 (as an echo). In response to receiving the reflection, the transducer 18 generates an electric signal which is provided to a microcontroller on a circuit board 22. The signal from the transducer 18 is processed in the microcontroller to generate, for example, a signal indicative of the volume of fluid 14 in the tank 12.

Figure 2:
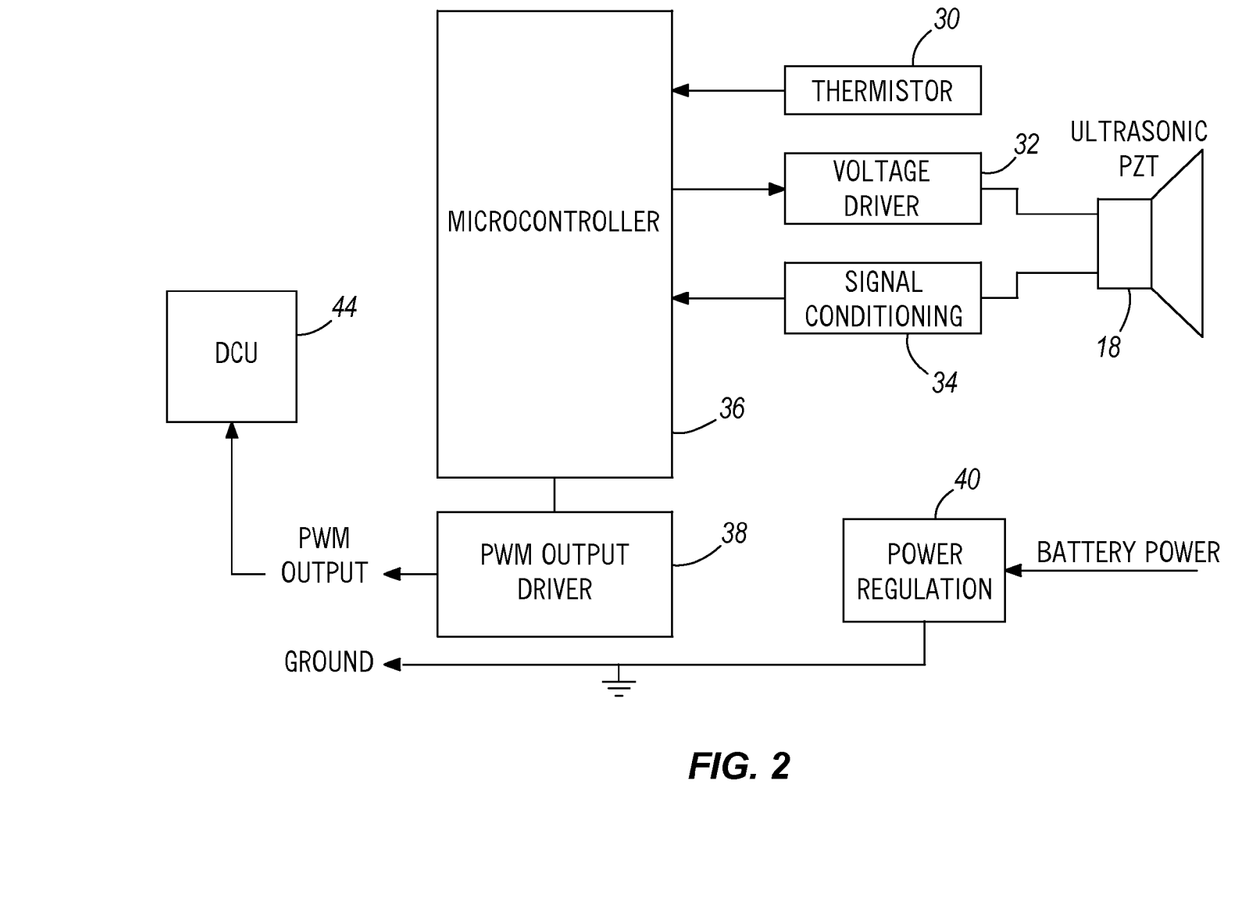
FIG. 2 is a schematic illustration of the circuitry of the ultrasonic level sensor illustrated in FIG. 1, including depictions of a piezoelectric transducer, a temperature sensor in the form of a thermistor, a voltage/transducer driver, a signal conditioning circuit, a microcontroller, an output driver, and a power regulation circuit.

FIG. 2 illustrates certain electrical components of the ultrasonic level sensor 10 including the piezoelectric transducer 18, a thermistor 30, a voltage driver 32, a signal conditioning circuit 34, a microcontroller 36, a PWM output driver 38, and a power regulation circuit 40. The microcontroller includes (or is connected to) memory such as RAM and ROM and executes software that can be stored in the RAM (particularly during execution), the ROM (on a generally permanent basis), or another non-transitory computer readable medium such as other memory or disc. If necessary, the microcontroller can be connected to such memory or a disc drive to read such software. A microprocessor or other programmable device with suitable memory and I/O devices could also be used.

Temperature information from the thermistor 30 (or other temperature sensor) is provided to the microcontroller 36 and is used by the microcontroller 36 to help it compensate for variations in the speed of sound that occur as a result of changes in temperature. On a regular basis (or as otherwise programmed), the microcontroller generates a transducer control signal which is delivered to the voltage driver 32. The voltage driver 32 amplifiers or otherwise conditions the control signal from microcontroller and provides the amplified signal to the transducer 18. When energized by the amplified signal, transducer 18 produces an output sound wave or, more particularly, an ultrasonic sound wave. In addition to generating sound waves, the transducer 18 also responds to sound waves (such as reflections or echos) by converting the received sound waves into electric signals (referred to as a "reflection signal"). Such signals are conditioned by signal conditioning circuit 34 and provided to the microcontroller 36. In response to a reflection signal, the microcontroller 36 generates an output signal indicative of the time lapsed between the moment the transducer sent out its ultrasonic signal (based on the transducer control signal) and the moment the transducer received a reflection of the ultrasonic signal (resulting in the generation of a reflection signal). This "time of flight" (the time between generation of the ultrasonic sound wave or ping and receipt of the reflection) can be used to determine the distance from the sensor 10 to the top surface 15. In other words, the height or level of the fluid in the tank can be determined. (The time between the transmitted ultrasonic pulse and the received echo is proportional to the distance the sound wave traveled through the liquid as expressed by the equation: Distance=Speed×(Time of Flight)/2). Provided other information is available and programmed into the microcontroller, the distance measurement may also be used to determine the volume of fluid in the tank 12.

The microcontroller 36 processes the reflection signal and generates an encoded digital signal. The encoded, digital signal is, in general terms, a PWM signal. The encoded, digital signal is provided (through an electrical connection) to the PWM output driver 38. As is described in more detail below, the PWM output driver 38 generates a PWM signal 42 (FIG. 4) including information regarding the time of flight as well as other information (discussed below). As its name implies, output driver 38 acts as an intermediary between the microcontroller 36 and other devices and, in particular, helps ensure that information or signals from the microcontroller are in an appropriate form for downstream use. However, the output driver 38 may not be necessary for all implementations and it may be possible to conduct an assessment on the signal generated by the microcontroller directly rather than the enhanced signal 42 generated by the output driver 38. The PWM signal 42 is provided to a second microcontroller, processor, or similar device. For example, in a vehicle with a diesel engine, the PWM signal is provided to a diesel engine control unit ("DCU") 44. The DCU 44 performs a diagnostic assessment (or evaluation or test) on the output signal of the PWM output driver 38. Like the microcontroller 36, the second microcontroller, processor, or DCU 44 includes (or is connected to) memory such as RAM and ROM and executes software that can be stored in the RAM (particularly during execution), the ROM (on a generally permanent basis), or another non-transitory computer readable medium such as other memory or disc. If necessary, the second microcontroller can be connected to such memory or a disc drive to read such software.

The evaluation performed on the PWM output signal of the driver 38 can determine the existence of a number of errors, including distance measurement errors. Distance measurement errors include at least two types: speed of sound ("SOS") errors and time measurement ("TM") errors.

Figure 3:
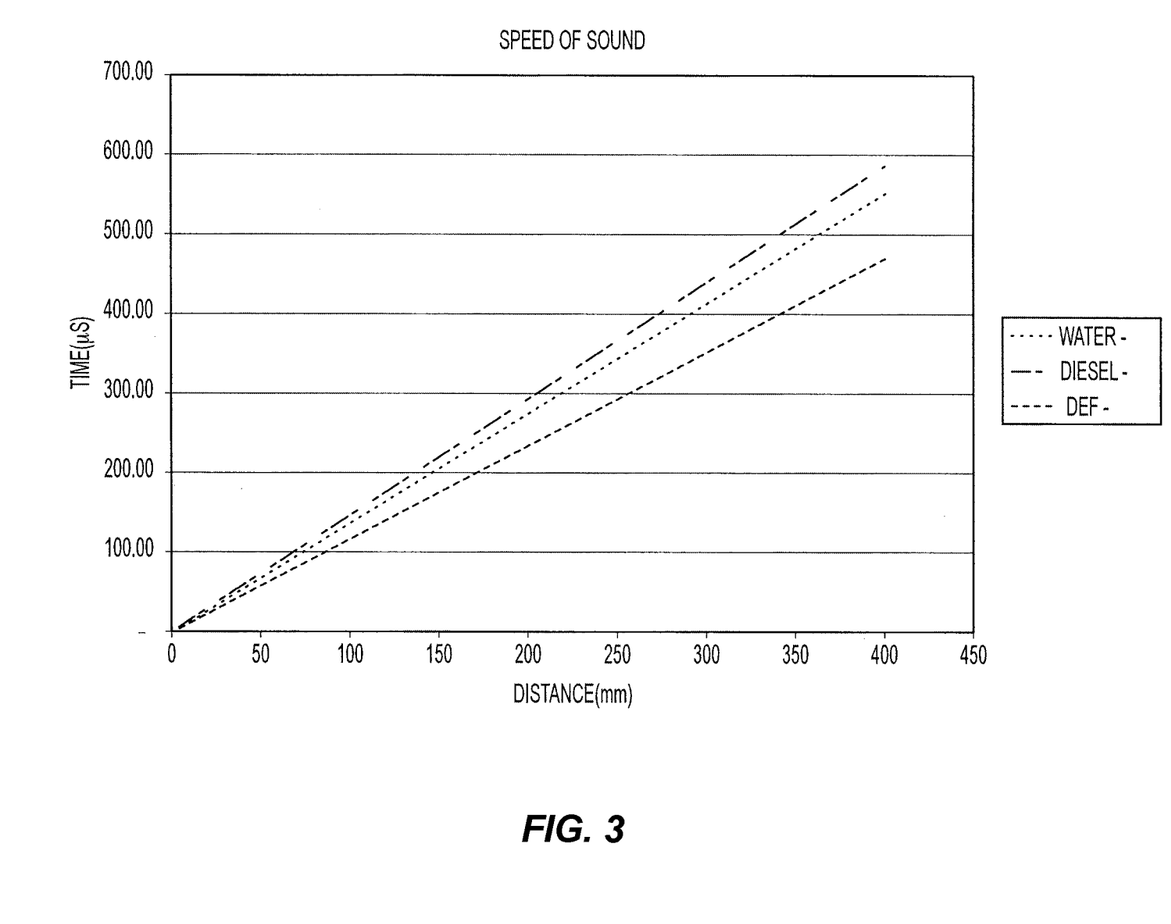
FIG. 3 is a graph illustrating differences in the time it takes sound to travel through water, diesel fuel, and diesel exhaust fluid ("DEF").

SOS errors can cause scaling errors in calculations performed by the microcontroller 36. SOS errors are more common when level sensing is performed in a tank full of fluid then when a tank is empty. SOS errors can occur when calculations or determinations are made based on incorrect assumptions, such as an assumption that a tank is filled with DEF, when in fact it is filled with a different liquid. FIG. 3 illustrates how time of flight measurements differ depending upon the type of liquid in which level sensing is performed. In particular, the speed of sound is affected by the density or specific gravity of the substance through which the sound travels. For example, if an ultrasonic level sensor is configured to perform level sensing on a DEF tank, but the tank is incorrectly or accidentally filled with water, when the tank is full the signal generated by the sensor will indicate a level that is above the highest level of the tank (e.g., the reading from the sensor might indicate a level of ~230 mm for a 200 mm tank). An assessment for this type of error can be referred to as a "over full plausibility check."

SOS errors can also occur due to incorrect temperature compensations. As noted above, the sensor 10 includes a thermistor or other temperature sensor and information from this sensor may be evaluated against temperature information from other sources of temperature information including, for example, temperature information provided to the DCU from, for example, a CAN bus. Thus, it is possible to determine whether the temperature information from the sensor 10 is within a predetermined range of the other temperature information available to the DCU and assess whether the temperature measurement provided by the thermistor 30 is plausible. A temperature compensation error check can be referred to as a temperature plausibility check.

Figure 4:
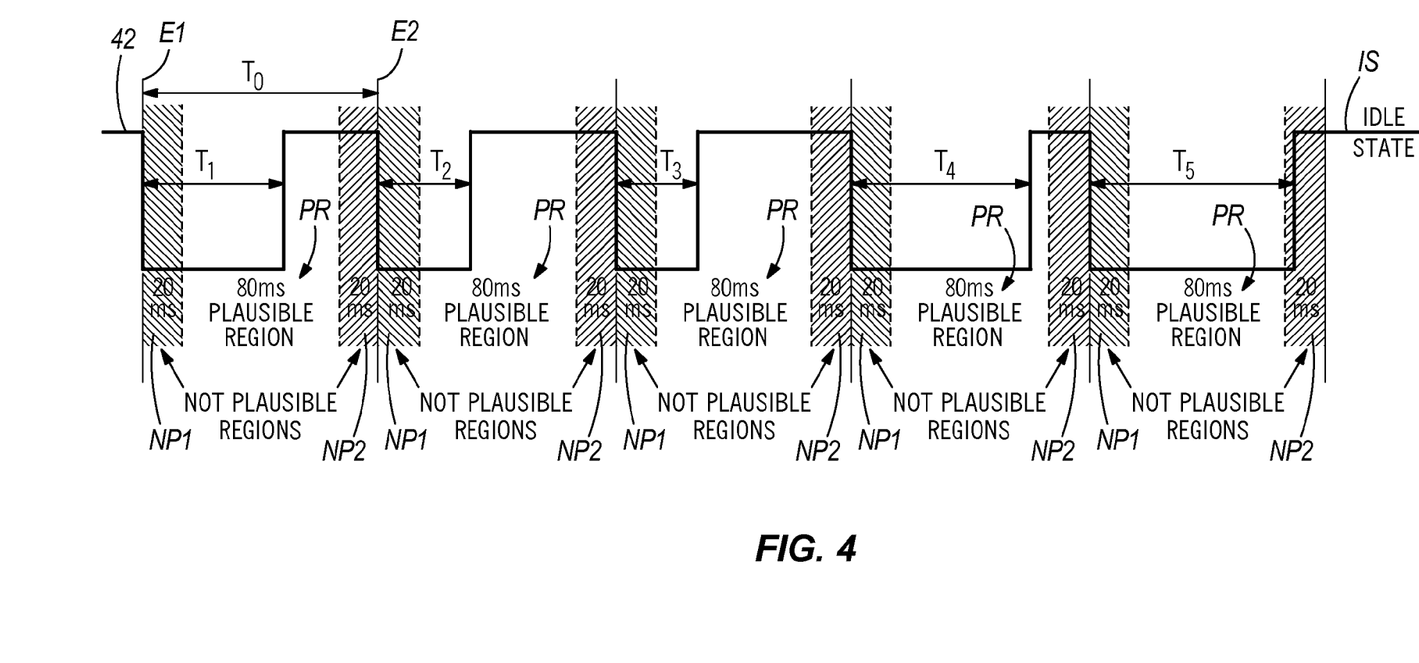
FIG. 4 is an illustration of a PWM output signal generated by the output driver circuit illustrated in FIG. 2 (as controlled by the microcontroller in FIG. 2).

As noted, initial time measurements (i.e., distance based on time of flight) are performed or determined by the microcontroller 36. The assessment of TM (or time measurement) errors is performed by the DCU 44. In particular, the DCU 44 performs a plausibility check on the time measurement accuracy using the PWM timing of the PWM signal 42.

As best seen by reference to FIG. 4, the PWM signal 42 includes a period, $T_0$, and a number of pulses: $T_1$, $T_2$, $T_3$, $T_4$, and $T_5$. Signal 42 is encoded in a manner such that pulse $T_1$ provides an indication of temperature, pulse $T_2$ provides an indication of fluid level (distance measurement), pulse $T_3$ provides an indication of quality (explained further below), pulse $T_4$ provides an indication of the status of the sensor 10, and, in the example provided, pulse $T_5$ is unused (but intended for future use). As a result of pulse $T_5$ being unused, its presence in the signal 42 is required, but its value is unimportant and, thus, ignored. After pulse $T_5$, the signal 42 has an idle state IS. The idle state IS may have a predetermined time, such as twice the length of $T_0$. Following the idle period a second signal 42 may be generated and sent to the DCU 44 (or other system) to provide updated information regarding the level of the fluid 14 in the tank 12.

The period $T_0$ is predetermined and represents, in general, a scaling factor and the longest possible time that any of the pulses in signal 42 may have. In the example shown, $T_0$ is set to 120 ms (the time between leading edges E1 and E2 in signal 42). A plausibility check on the PWM signal 42 may be performed by determining the time (or width) of the pulses, including for example, pulse $T_2$. If the time of $T_2$ exceeds $T_0$, then a time measurement error has occurred. Additional testing may be performed on the signal 42 based on the time of the pulses. The time of each pulse may be examined to determine whether the time (or width) falls within one of two implausible or not plausible regions, NP1 and NP2, for each period of the signal 42. In the example shown, each not plausible region has a width of 20 ms. Each pulse ($T_1$, $T_2$, $T_3$, and $T_4$ ($T_5$ ignored)), is evaluated to see if its width falls within one of the regions NP1 or NP2. In general, a pulse falling with the region NP1 is too short (or narrow) and a pulse falling within region NP2 is too long (or wide). The region between NP1 and NP2 is a plausible region, PR.

As noted, signal 42 is an encoded signal. In one example, encoding is implemented as follows. The percentage of time $T_1$ from 20 ms to 100 ms indicates the temperature from −40° to 85° C., according to the formula: Temperature=($T_1$−20)/80 *125−40 degrees C. The percentage of time $T_2$ from 20 ms to 100 ms indicates the percentage of fluid level in tank 12, according to the formula: Level=($T_2$−20)/80 percent full. The percentage of time $T_3$ from 20 ms to 100 ms indicates the speed of sound of the fluid through which the ultrasonic signal is sent (and is used for determining quality) according to the following formula: SOS=($T_2$−20)/80*5+500 meters/second. "Quality" is most often an indication of the type of liquid present within the tank and $T_3$ can be evaluated against speed-of-sound or specific-gravity values stored in the memory of the microcontroller 36. As noted, $T_5$ is a spare pulse with which additional information could be encoded in the signal 42, if desired. $T_4$ provides an indication of the status of the sensor 10, and is discussed in the next paragraph.

As shown in Table 1, the sensor 10 operates in a number of states: State 1, State 2, and State 3. As shown in the key for Table 1, State 1 provides an indication regarding whether the sensor is outputting a valid level measurement, State 2 provides an indication regarding the quality of the sensor output, and State 3 provides an indication regarding the operating or operational life of the sensor (e.g., number of hours in use). These states are determined by the microcontroller 36 and not the DCU 44.

TABLE 1

| Sensor Status | | | | |
|---|---|---|---|---|
| Ultrasonic Sensor | | | PWM-Signal | |
| State 1 | State 2 | State 3 | Output in % | $T_4$ in ms |
| 0 | 0 | 0 | 10 | 28 |
| 0 | 0 | 1 | 20 | 36 |
| 0 | 1 | 0 | 30 | 44 |
| 0 | 1 | 1 | 40 | 52 |
| 1 | 0 | 0 | 50 | 60 |
| 1 | 0 | 1 | 60 | 68 |
| 1 | 1 | 0 | 70 | 76 |
| 1 | 1 | 1 | 80 | 84 |

State 1: level invalid
State 2: quality invalid
State 3: life bit (toggled each transmission protocol)
Active = 1, not active = 0; (undefined state(s) = 0)

For the sake of brevity, only a selected number of sensor states from Table 1 are described herein. If the sensor 10 is operating in State 1 (or State 1 is active), a level measurement outside of predetermined bounds has been made. For example, the microcontroller 36 could send the transducer control signal to the transducer 18, but no reflection signal is received (within a predetermined amount of time). Such a condition could occur due to bonding failures in the transducer (e.g., components within the transducer becoming unglued) or electrical connection failures. Both of these failures result in what is referred to as a "no echo" condition. Failures of the voltage driver 32 and signal conditioning circuit 34 can also result in a "no echo" condition.

The "no echo" condition is reported to the DCU 44 (as encoded in $T_4$). The DCU performs a plausibility check on the "no echo" condition. A circumstance in which no echo or reflection would be present is when, for example, the DEF is frozen or the vehicle is on an incline. The DCU plausibility check requires the "no echo" condition to persist over several hours to avoid false indications which can arise from situations such as those just described (the vehicle operates at an angle and operation of the sensor 10 when the DEF is frozen).

In addition to the failures or malfunctions mentioned, additional failures can occur. For example, it is possible that the microcontroller 36 may malfunction. Depending on the nature of the microcontroller malfunction, the signal 42 may not be generated (a PWM signal absence). Alternatively, a microcontroller malfunction could cause a time reference shift. In other words, pulses in the digital signal created by the microcontroller could fall outside predetermined timing constraints such as $T_0$. Time reference shifts can be detected by the DCU 44 using the PWM timing previously described (e.g., pulses occurring in zones NP1 or NP2). Because these time reference shifts can be detected, the sensor 10 is said to have immunity from such shifts. Still other failures could occur due to a malfunction of the output driver 38 or power regulation circuit 40. If a failure of the output driver 38 occurs, a loss of the signal 42 occurs (in most instances). Thus, the signal 42 is not provided to the DCU 44. Similarly, a failure of the power regulation circuit 40 commonly results in a loss of PWM signal 42 to the DCU 44.

In typical diagnostics systems, signals are evaluated against reference values (without further analysis). However, the use of reference values alone cannot, in general, effectively differentiate between the various types of errors that may occur. For example, it is not, in general, possible (by use of a reference value) to isolate whether a sensor is experiencing a time reference shift failure or the wrong media or fluid has been added to the tank 12. Similarly, use of a reference value alone is generally insufficient to isolate or distinguish "no echo" conditions from sensor failures or from angled or frozen operation.

Figure 5:
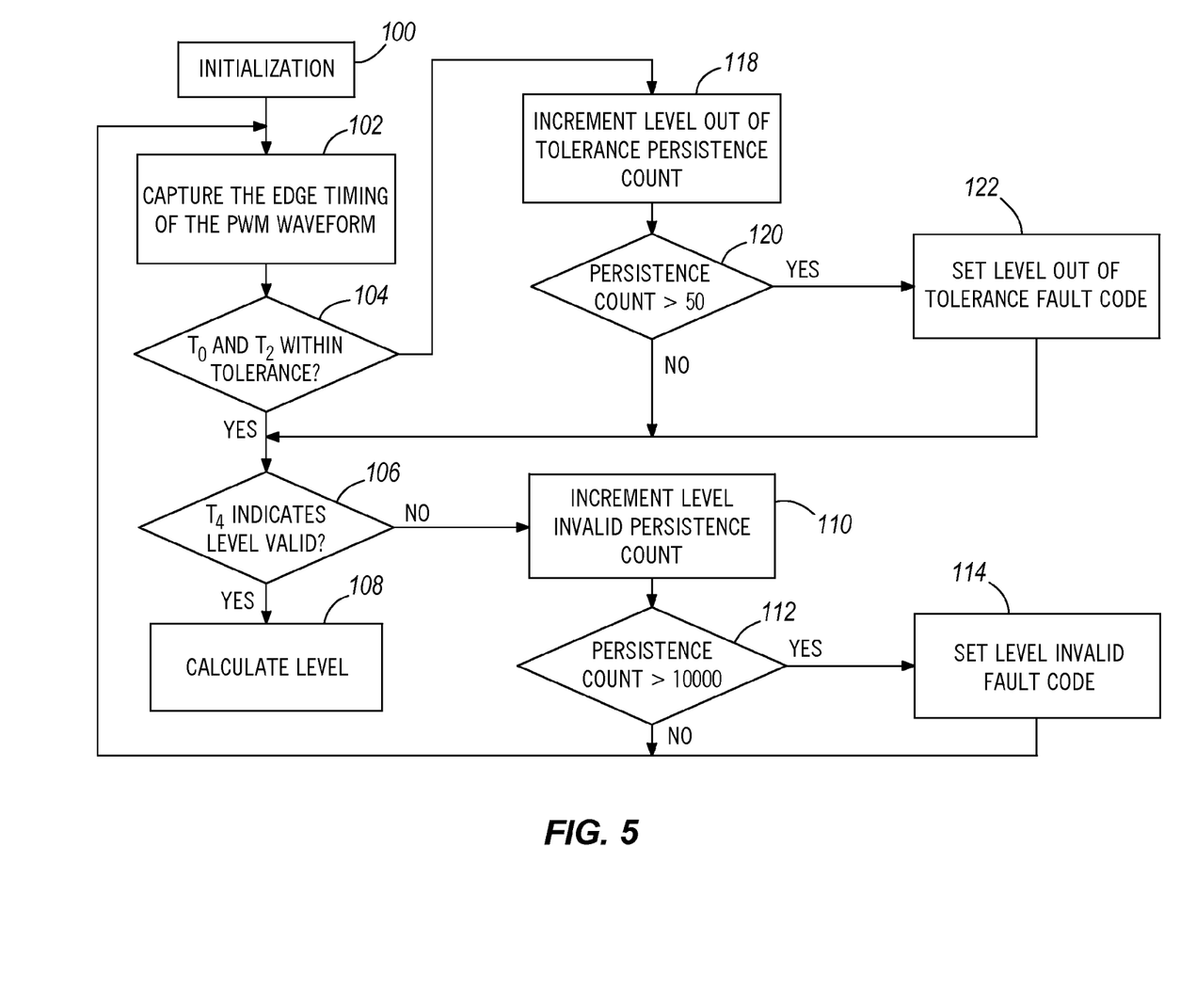
FIG. 5 is a flow chart illustrating the operation of software executed by a microcontroller or similar device for performing a diagnostic test or assessment on an output signal generated by the output driver.
Figure 6:
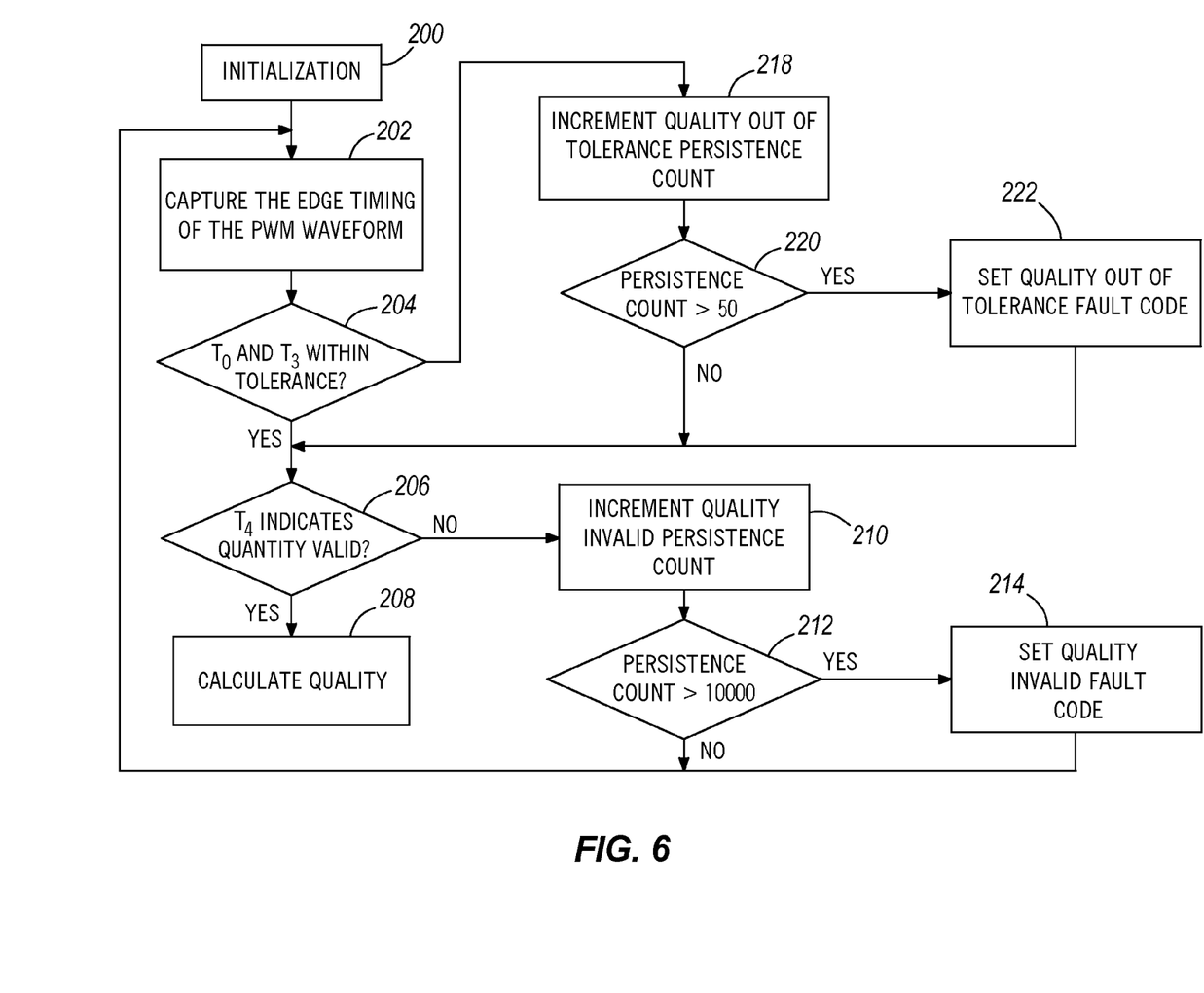
FIG. 6 is a second flow chart illustrating the operation of software executed by a microcontroller or similar device for performing a diagnostic test or assessment on an output signal generated by the output driver.

FIGS. 15 and 16 are flow charts illustrating diagnostic assessments carried out by the DCU 44. As noted above, although the DCU 44 is used in some embodiments (particularly, in embodiments where the sensor 10 is installed in a diesel engine vehicle) the DCU acts as an assessment device or module and devices other than the DCU 44 such as a standalone microcontroller or microprocessor or even other vehicle systems could be programmed to assess the signal 42.

The process illustrated in FIG. 5 begins at initialization step 100. The DCU 44 captures the edge timing of PWM signal 42, as shown at step 102. The DCU 44 then determines whether $T_0$ and $T_2$ fall within predetermined tolerances (e.g., plausible region PR) (step 104). Next, the DCU 44 evaluates $T_4$ to determine whether the pulse indicates a valid level. If so, the DCU calculates a fluid level for the tank 12 (as shown in step 108). Otherwise, the DCU increments an invalid level counter (as shown in step 110). If the invalid level counter is greater than 10,000 (or another predetermined threshold) (step 112), then an invalid level fault code is set (at step 114). Evaluation of the PWM signal 42 then continues back at step 102.

If $T_0$ and $T_2$ fall outside of the predetermined tolerances (as determined in step 104), a level-out-of-tolerance counter is incremented (as shown in step 118). If the counter is greater than 50 (or another predetermined threshold) (step 120), then a level-out-of-tolerance fault code is set (step 122). Otherwise, processing continues with step 106.

The process illustrated in FIG. 6 begins at initialization step 200. The DCU 44 captures the edge timing of PWM signal 42, as shown at step 202. The DCU 44 then determines whether $T_0$ and $T_3$ fall within predetermined tolerances (e.g., plausible region PR) (step 204). Next, the DCU 44 evaluates $T_4$ to determine whether the pulse indicates a valid level. If so, the DCU 44 calculates a quality for the fluid in the tank 12 (as shown in step 208). Otherwise, the DCU increments an invalid quality counter (as shown in step 210). If the invalid quality counter is greater than 10,000 (or another predetermined threshold) (step 212), then an invalid quality fault code is set (at step 214). Evaluation of the PWM signal 42 then continues back at step 202.

If $T_0$ and $T_3$ fall outside of the predetermined tolerances (as determined in step 204), a quality out of tolerance counter is incremented (as shown in step 218). If the counter is greater than 50 (or another predetermined threshold) (step 220), then a quality out of tolerance fault code is set (step 222). Otherwise, processing continues with step 206.

Thus, the invention provides, among other things, methods and devices for performing a diagnostic assessment on an ultrasonic level sensor. Various features and advantages of the invention are set forth in the following claims.

What is claimed is:

1. An ultrasonic sensing system comprising:
   an ultrasonic sensor including
      a microcontroller,
      a transducer electrically connected to the microcontroller and configured to generate an ultrasonic signal and to receive a reflection of the ultrasonic signal from a surface of a fluid, and
      a driver electrically connected to the microcontroller and configured to output a pulse-width modulated (PWM) signal based on the reflection, the PWM signal including:
         a period, and
         a plurality of pulses including a first pulse having a first pulse width, and encoding a first predetermined parameter based on the first pulse width and a second pulse, having a second pulse width, and encoding a second predetermined parameter based on the second pulse width, the second predetermined parameter different from the first predetermined parameter; and
   a processor configured to receive the PWM signal from the driver and perform a diagnostic assessment of the ultrasonic sensor based on the period of the PWM signal and the widths of the plurality of pulses of the PWM signal.

2. The ultrasonic sensing system of claim 1, wherein the first pulse encodes a level of the fluid, and a the second pulse encodes a status of the ultrasonic sensor.

3. The ultrasonic sensing system of claim 2, wherein the status of the ultrasonic sensor indicates whether the level of the fluid encoded in the PWM signal is a valid level value.

4. The ultrasonic sensing system of claim 1, wherein the plurality of pulses includes a third pulse encoding a temperature of the fluid.

5. The ultrasonic sensing system of claim 1, wherein the microcontroller detects a temperature of the fluid and compensates for variations in a speed of sound through the fluid based on the temperature to calculate a level of the fluid.

6. The ultrasonic sensing system of claim 2, wherein the plurality of pulses further includes a fourth pulse encoding a speed of sound through the fluid.

7. The ultrasonic sensing system of claim 6, wherein the status of the ultrasonic sensor indicates whether the speed of sound of the fluid encoded in the PWM signal is a valid speed value within a predetermined speed of sound tolerance.

8. The ultrasonic sensing system of claim 2, wherein the status of the ultrasonic sensor includes a life bit that is toggled relative to a previous status of the ultrasonic sensor to indicate that the transducer has been operated for an additional period of time.

9. The ultrasonic sensing system of claim 1, wherein, to perform the diagnostic assessment, the processor:
   determines whether the first pulse of the plurality of pulses is within a first plausible region of a time constraint;
   determines whether the second pulse of the plurality of pulses is within a second plausible region of the time constraint; and
   detects a time reference shift based on at least one of the first pulse being outside of the first plausible region and the second pulse being outside of the second plausible region.

10. The ultrasonic sensing system of claim 9, wherein, to perform the diagnostic assessment, the processor further:
receives subsequent PWM signals;
detects subsequent time reference shifts based on pulses within the subsequent PWM signals; and
determines that a fault has occurred upon detecting a predetermined amount of time reference shifts.

11. A method of performing a diagnostic assessment of an ultrasonic sensor that measures a fluid level, the method comprising:
generating a PWM signal based on a reflection of an ultrasonic signal output by the ultrasonic sensor so that the PWM signal has
a period, and
a plurality of pulses including a first pulse having a first pulse width, and encoding a first predetermined parameter based on the first pulse width and a second pulse, having a second pulse width, and encoding a second predetermined parameter based on the second pulse width, the second predetermined parameter different from the first predetermined parameter;
receiving the PWM signal at a processor;
performing, via the processor, the diagnostic assessment of the ultrasonic sensor based on the period of the PWM signal and the widths of the plurality of pulses of the PWM signal.

12. The method of claim 11, wherein performing the diagnostic assessment includes:
determining whether the first pulse of the plurality of pulses is within a first plausible region of a time constraint;
determining whether the second pulse of the plurality of pulses is within a second plausible region of the time constraint; and
detecting a time reference shift based on at least one of the first pulse being outside of the first plausible region and the second pulse being outside of the second plausible region.

13. The method of claim 12, further comprising
receiving subsequent PWM signals;
detecting subsequent time reference shifts based on pulses within the subsequent PWM signals; and
determining a fault has occurred upon detecting a predetermined amount of time reference shifts.

14. The method of claim 11, wherein a the first pulse encodes the fluid level based on the reflection of the ultrasonic signal.

15. The method of claim 14, wherein a the second pulse encodes a status of the ultrasonic sensor that indicates whether the fluid level encoded in the first pulse is a valid level value.

16. The method of claim 15, wherein a third pulse of the plurality of pulses encodes a temperature of the fluid and the ultrasonic sensor compensates, using the temperature, for variations in a speed of sound through the fluid to calculate the fluid level.

17. The method of claim 15, wherein a fourth pulse of the plurality of pulses encodes a speed of sound through the fluid and the status of the ultrasonic sensor indicates whether the speed of sound of the fluid encoded in the fourth pulse is a valid speed value within a predetermined speed of sound tolerance.

* * * * *